(12) United States Patent
Chandler

(10) Patent No.: US 6,977,173 B2
(45) Date of Patent: Dec. 20, 2005

(54) APPARATUS AND METHOD FOR ANALYTE DETECTION

(75) Inventor: Howard Milne Chandler, Yarmouth, ME (US)

(73) Assignee: Enterix, Inc., Edison, NJ (US)

( * ) Notice: Subject to any disclaimer, the term of this patent is extended or adjusted under 35 U.S.C. 154(b) by 388 days.

(21) Appl. No.: 09/765,217

(22) Filed: Jan. 18, 2001

(65) Prior Publication Data

US 2001/0004532 A1 Jun. 21, 2001
US 2005/0158878 A9 Jun. 21, 2001

Related U.S. Application Data

(60) Division of application No. 09/166,599, filed on Oct. 5, 1998, now Pat. No. 6,221,678, which is a continuation-in-part of application No. 08/944,858, filed on Oct. 6, 1997, now Pat. No. 6,271,046.

(30) Foreign Application Priority Data

May 11, 1998 (AU) .......................................... PP3461/98

(51) Int. Cl.$^7$ ............................................... C12M 3/00
(52) U.S. Cl. .................... 435/287.1; 422/50; 422/55; 422/56; 422/57; 422/58; 422/61; 435/7.21; 435/7.22; 435/7.23; 435/7.24; 435/287.2; 435/287.7; 435/287.9; 435/288.5; 435/805; 435/810; 435/970; 436/64; 436/66; 436/67; 436/164; 436/169; 436/514; 436/518; 436/530; 436/805; 436/810; 436/813
(58) Field of Search ................................. 422/50, 55–58, 422/61; 435/7.21, 7.22, 7.23, 7.24, 282.1, 282.2, 287.7, 287.9, 288.5, 805, 810, 970; 436/66, 67, 64, 164, 169, 514, 518, 530, 805, 810, 813

(56) References Cited

U.S. PATENT DOCUMENTS

| | | |
|---|---|---|
| 3,996,006 A | 12/1976 | Pagano |
| 4,225,557 A | 9/1980 | Hartl et al. |
| 4,789,629 A | 12/1988 | Baker et al. |
| 5,064,766 A | 11/1991 | Wardlaw et al. |
| 5,100,619 A | 3/1992 | Baker et al. |
| 5,106,582 A | 4/1992 | Baker |
| 5,171,528 A | 12/1992 | Wardlaw et al. |
| 5,171,529 A | 12/1992 | Schreiber |
| 5,182,191 A | 1/1993 | Fan et al. |
| 5,238,847 A | 8/1993 | Steinbiss et al. |
| 5,591,645 A | 1/1997 | Rosenstein |
| 5,622,871 A * | 4/1997 | May et al. .................. 436/514 |
| 5,712,172 A * | 1/1998 | Huang et al. ............... 436/518 |
| 5,747,351 A | 5/1998 | Hemmati |
| 5,846,838 A * | 12/1998 | Chandler .................... 436/514 |

* cited by examiner

*Primary Examiner*—Christopher L. Chin
(74) *Attorney, Agent, or Firm*—Pierce Atwood; Kevin M. Farrell

(57) ABSTRACT

Disclosed is a testing device and methods for the identification of an analyte of interest in a sample. In a preferred embodiment, the testing device includes a front panel having at least one sample application aperture; a rear panel having at least one solvent application aperture; a sample collection matrix disposed between the rear panel and the front panel, the sample collection matrix being in communication with the sample and solvent application apertures of the front and rear panels; and at least one insertable test strip containing a reagent enabling detection of the analyte of interest.

11 Claims, 4 Drawing Sheets

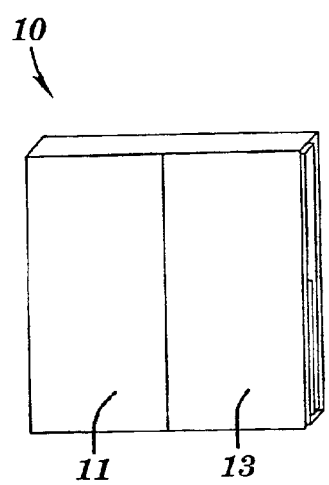
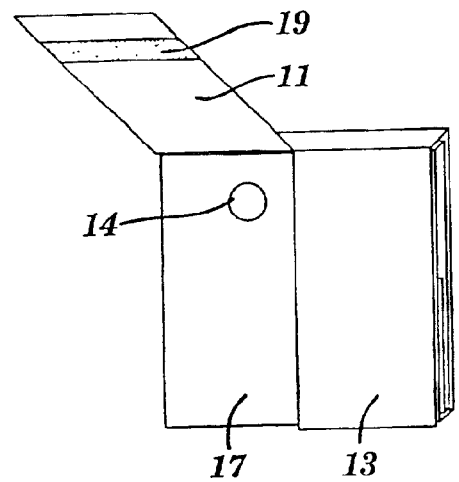
FIG. 1A
FIG. 1B
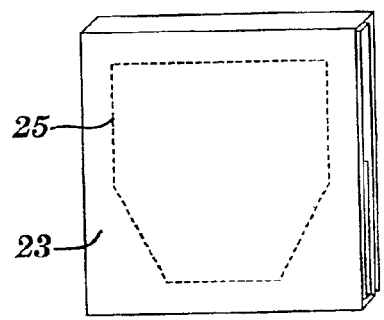
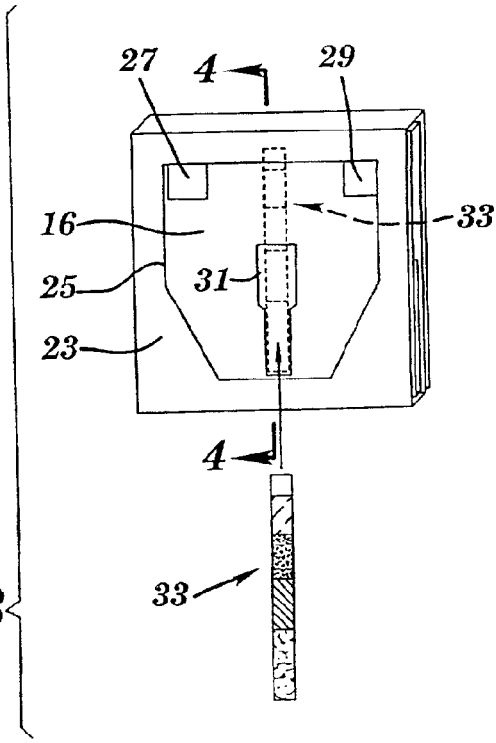
FIG. 2A
FIG. 2B

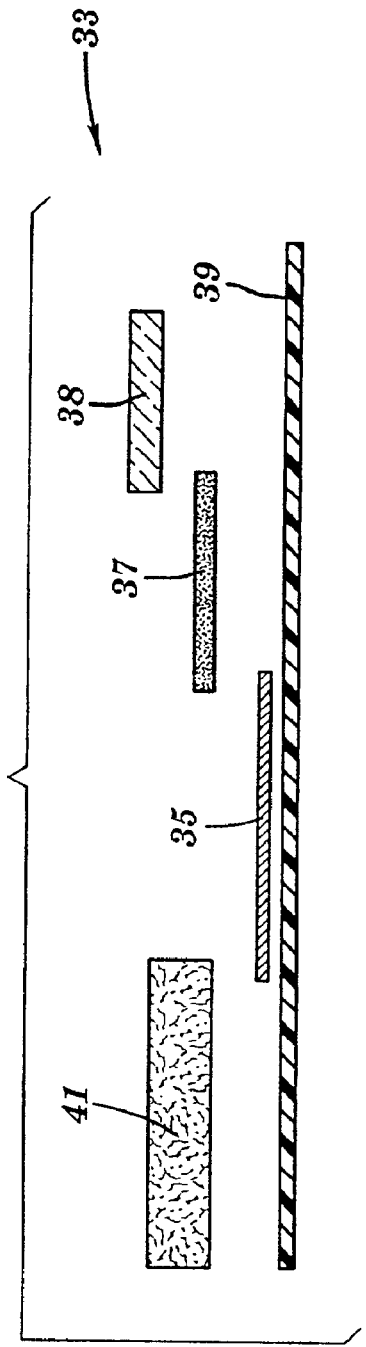
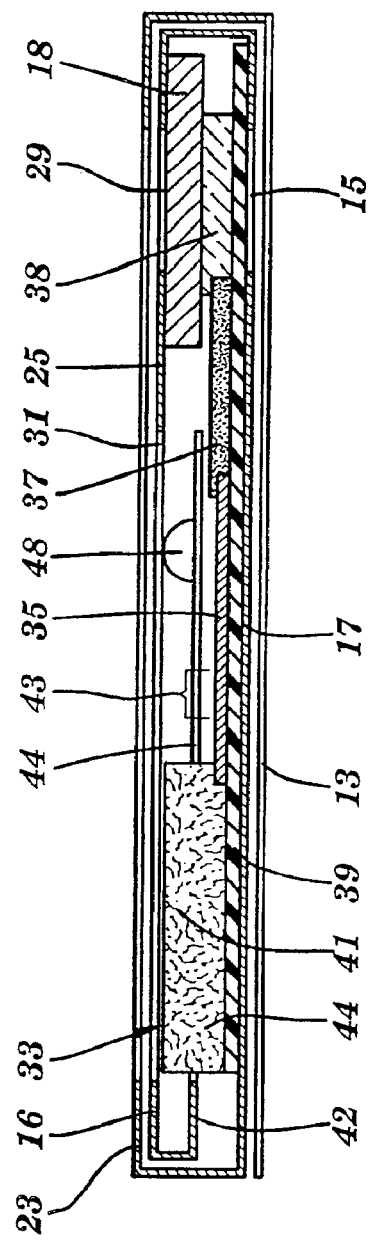

APPARATUS AND METHOD FOR ANALYTE DETECTION

The present application is a Division of U.S. Application No. 09/166,599, filed on Oct. 5, 1998, now U.S. Pat. No. 6,221,678 issued Apr. 24, 2001, which is a Continuation-in-part of application U.S. Application No. 08/944,858, filed on Oct. 6, 1997, now U.S. Pat. No. 6,271,046 issued Aug. 7, 2001.

FIELD OF THE INVENTION

This invention relates to an apparatus and method for the direct or indirect detection of an analyte in a sample, particularly but not exclusively for detection of an analyte in a biological sample. The present invention is particularly useful for ascertaining the health status of a human or other animal or a plant or other life form or the environmental status of a geographical or industrial location by ascertaining the presence or absence of an analyte.

BACKGROUND OF THE INVENTION

A variety of diagnostic devices have been developed for the detection of an analyte of interest in a sample. In those devices in which sample collection and testing functions are non-linked, the transfer of collected sample to testing apparatus introduces a potential source of error. In those devices in which sample collection and testing functions are linked, the devices are dedicated in their entirety to the detection of a particular analyte and are not easily adaptable to a wide range of analyte detection.

The issue of self-diagnosis of serious disease such as cancer or AIDS has been considered at length. There is general consensus that self-diagnosis of such disease states is not preferred. Rather, it is generally accepted that a positive diagnosis for such a disease state should be communicated by a doctor, together with information relating to the availability of counselling services.

With respect to mammalian systems (e.g. humans), samples amenable to analysis using the testing device of the present invention include biological fluids (e.g. blood, urine, semen, saliva, etc.) or excrements. Such biological fluids can carry a variety of analytes, the presence of which can be diagnostic for a particular disease state. An important example of a disease state which is characterised by the presence of a disease-specific analyte in a biological fluid is Acquired Immunodeficiency Syndrome (AIDS). Using the device and method of the present invention, the presence of antibodies specific for the Human Immunodeficiency Virus (HIV), the causative agent of AIDS, in a blood sample are detectable.

The application of the subject invention to the detection of disease states in humans is of primary importance. However, in addition to use in the context of the diagnosis of serious disease states, the present invention is also useful in a variety of other contexts. Applications in connection with the analysis of microbes, plants, animals, food and water are all anticipated.

For example, ground water samples can be analysed for the presence of contaminants such as atrazine. Food, such as ground beef, can be analysed for the presence of contamination by bacteria such as $E.\ coli$. In the plant kingdom, the present invention can be applied to the analysis of, for example, pollen, spores and plant vascular fluids. Generally speaking, the only requirement for detection using the device and method of the present invention is that the analyte of interest should be soluble or suspendible in an aqueous solution.

The device and method of the present invention are particularly useful for the detection of occult gastrointestinal bleeding. The detection of occult gastrointestinal bleeding is a common method for screening for colo-rectal cancer. Commonly referred to as the faecal occult blood (FOB) test, a variety of formats are known in the art (see e.g., U.S. Pat. Nos. 3,996,006; 4,225,557; 4,789,629; 5,064,766; 5,100,619; 5,106,582; 5,171,528; 5,171,529; and 5,182,191).

The majority of test formats are based on the chemical detection of heme groups present in stool as a breakdown product of blood. In such tests, the pseudoperoxidase nature of the heme group is used to catalyse a colorimetric reaction between an indicator dye and peroxide. The oxygen sensitive dye can be gum guaiac, orthodianisidine, tetramethylbenzidine, or the like with guaiac being preferred.

While guaiac-based FOB tests are inexpensive and simple to use, there are disadvantages associated with their use. For example, guaiac-based tests indicate only the presence of peroxidase and pseudoperoxidase compounds, such as heme, that are present in a sample. Consequently, these tests are not specific for human blood, and are therefore subject to false-positive results if the patient's stool is contaminated with cross-reacting compounds. Such cross reacting compounds include, for example, non-human blood breakdown products from under-cooked meat, certain vegetable products, and some drugs. According to currently accepted medical practice, a patient demonstrating a positive result should then undergo a flexible sigmoidoscopy or colonoscopy to identify the source of the bleeding in the colon or rectum. These procedures can be invasive, medically complicated, and expensive. To minimize false positive reactions and the unnecessary follow-up procedures, guaiac based FOB tests require a restrictive diet for up to three days prior to testing.

Recent reports in the literature (Allison, et al. N. Eng. J. Med. 344: 155–159 (1996); and Favennec et al., Annales de Biologie Clinique 50: 311–313 (1992)) have suggested that screening by guaiac and confirmation of positive results by an immunological test, with absolute specificity for human blood, would increase the value of FOB test results. By this means, only those patients with confirmed gastrointestinal bleeding would be subjected to the expensive follow-up procedures, leading to significant savings in health care delivery cost and reduced inconvenience to the patient.

The present invention relates to a device which is useful inter alia for the detection of any aqueous soluble or suspendible analyte which is detectable, for example, on the basis of immunological and/or chemical properties. An example of an analyte detected by its immunological properties includes, but is not limited to, an immune interacting molecule such as an antigen, hapten, immunoglobulin or T-cell derived antigen binding molecule. An example of an analyte detected by chemical properties includes an enzyme, catalyst or ligand. Thus, with respect to FOB tests, the device of the present invention can be adapted to either guaiac-based testing, or immunological testing. The preferred format for immunological testing is immunochromatography. This format is described generally in U.S. Pat. Nos. 5,591,645 and 5,622,871, the disclosures of which are incorporated herein by reference.

Prior to discussing the invention in greater detail, a brief review of the immunochromatography process will be provided to establish certain principles. To detect an analyte of interest by immunochromatography, two binding reagents which bind specifically and noncompetitively to the analyte of interest may be employed. A first specific binding reagent is labelled and is free to migrate. When introduced to a sample to be tested for the presence of the analyte of interest, the first specific binding reagent binds to the analyte of interest, if present. The second specific binding reagent is immobilized in a detection zone on a liquid-conductive solid phase material, the detection zone being remote and downstream from the location of initial contact between the first binding reagent and the analyte of interest. A solvent front carrying the mobile first specific binding reagent complexed with analyte of interest (if present) migrates along the liquid-conductive solid phase material through the detection zone. If analyte is present in the sample, the immobilised second specific binding reagent binds the analyte thereby forming an immobilised sandwich complex comprising the first specific binding reagent (which is labelled), the analyte of interest, and the second specific binding reagent (which is immobilised). Detection of the label immobilised in the detection zone is indicative of the presence of analyte of interest in the sample. In most embodiments, the first and second specific binding reagents are either polyclonal or monoclonal antibodies.

SUMMARY OF THE INVENTION

The present invention relates to a testing device and methods for the identification of an analyte of interest in a sample. The testing device offers a variety of advantages over prior art devices. An important feature of the testing device of the present invention is that the single device serves a collection and testing function. However, the testing function is not linked to collection. That is, the collection of a sample (e.g. by a patient in their home) and application to the testing device does not yield a test result. In order to determine the test result, an insertable testing element must be inserted into the device, and if the sample has previously been dried or desiccated the sample must be rehydrated. In practice, the testing element will not be provided with the device and, therefore, the patient will not self-diagnose at home.

In one aspect, the present invention provides a testing device for the identification of an analyte of interest in a sample, comprising:
(a) a sample application matrix adapted for receipt of a sample, and
(b) at least one insertable testing element adapted for communication with the sample application matrix such that components of the sample are carried from the sample application matrix to the testing element or elements.

Preferably, the sample is a liquid containing sample. The sample may itself be a liquid or it may be in particulate or solid form like hydrates prior to testing.

In accordance with this invention, the or each testing element is adapted to be inserted into the test device, so that the testing element is in liquid-conductive communication with the sample application matrix as described above.

As used herein, the term "liquid-conductive communication" shall be taken to mean that a liquid applied to a sample application matrix is capable of being in liquid-conductive communication with a test element under sufficient conditions of hydration In a preferred but not essential aspect of this invention, the testing device is adapted so that a sample applied to the device (for example, by a patient in their home) may be dried or desiccated on the sample application matrix. Accordingly, in this aspect, the testing device comprises:
(a) a sample application matrix adapted for:
    (i) receipt of a liquid-containing sample;
    (ii) desiccation of the liquid-containing sample in situ; and
    (iii) rehydration of the desiccated liquid containing sample for transfer to a testing element; and
(b) at least one insertable testing element adapted for liquid-conductive communication with the sample application matrix such that upon rehydration, resolubilised or resuspended components of the liquid-containing sample are carried from the sample application matrix to the testing element or elements.

In one embodiment of this invention, the testing device may comprise:
(a) a front panel having at least one sample application aperture therein;
(b) a rear panel having at least one buffer application aperture therein;
(c) a sample application matrix disposed between the rear panel and the front panel, the sample application matrix being in communication with the sample and buffer application apertures of the front and rear panels; and
(d) at least one insertable testing element adapted for liquid-conductive communication with the sample application matrix such that components of the liquid-containing sample are carried from the sample application matrix to the testing element or elements.

Preferably, the or each insertable testing element comprises a reagent or reagents enabling detection of the analyte of interest.

The present invention also provides a method for conducting an assay for identifying an analyte of interest in a sample, comprising;
(a) providing a testing device comprising a sample application matrix adapted for receipt of a liquid containing sample;
(b) applying a liquid-containing sample to the sample application matrix;
(c) inserting into the testing device at least one insertable testing element in liquid-conductive communication with the sample application matrix such that components of the liquid-containing sample are carried from the sample application matrix to the testing element or elements; and
(d) determining the test results.

In one embodiment, the method comprises:
(a) providing a testing device comprising:
    (i) a front panel having at least one sample application aperture therein;
    (ii) a rear panel having at least one buffer application aperture therein; and
    (iii) a sample application matrix disposed between the rear panel and the front panel, the sample application matrix being in communication with the sample and buffer application apertures of the front and rear panels;
(b) applying a liquid-containing sample to the sample application matrix;
(c) inserting into the testing device at least one insertable testing element in liquid-conductive communication with the sample application matrix, for example an immunochromatographic test strip, comprising a liquid-conductive solid phase material and a backing material, the insertable immunochromatographic test strip having a contact zone which, following insertion, contacts the sample application matrix and conducts a solvent front from the sample application matrix through a detection zone which contains a specific binding reagent, the detection zone being spatially distinct from the contact zone;
(d) applying buffer to the sample application matrix; and
(e) determining the test results, for example by observing immunochromatographic results.

Throughout this specification, unless the context requires otherwise, the word "comprise", and or variations such as "comprises" or "comprising", will be understood to imply the inclusion of a stated integer or step or group of integers or steps but not the exclusion of any other integer or step or group of integers or steps.

Preferred embodiments of the present invention are comprised of a housing having a front panel and a rear panel; a sample application matrix disposed between the front panel and the rear panel, the housing being adapted for application of the sample to the sample application matrix; a testing element insertion window in the housing; and at least one insertable testing element which, when inserted, communicates with the sample application matrix. In preferred embodiments, at least one aperture is provided in the housing which is in direct communication with the sample application matrix. This aperture provides access to the sample application matrix for the purpose of applying sample.

In other embodiments, multiple apertures in the housing are provided for sample application thereby facilitating, for example, the testing of samples collected on multiple days in a single test or alternatively, the testing of multiple samples collected on a single day in a single test.

In an important embodiment of the present invention, the device comprises two or more insertable testing elements each of which, when inserted, communicates with the sample application matrix. In this embodiment, the testing elements may be either the same or they may be different. In the former case, replicate tests may be carried out on the sample or samples applied to the sample application matrix. In the latter case, different tests may be carried out on the same sample or samples applied to the sample application matrix. By way of example, in FOB testing for screening for colorectal cancer, one insertable testing element may be a guaiac-based FOB test element, whilst another insertable testing element may be an immunochromatographic test element.

The housing is preferably constructed of a flexible, creasable, water-resistant material. Examples of such material include coated paper or card stock, or thin plastic sheet stock. In preferred embodiments, the housing is constructed from a single sheet of stock which is folded to create a plurality of panels or faces, including the front panel and the rear panel. Alternatively, multiple webs may be laminated together to construct a similar structure.

The sample application matrix is disposed between the front and rear panel and may be attached to either of the two panels with a non-soluble adhesive. The selection of a material for the sample application matrix is, to some degree, dependent upon the type of sample to be applied. Generally speaking, however, an open-celled, chemically inert matrix (e.g., porous plastic, filter paper, glass fiber) is preferred. Such an open-celled matrix allows rapid and complete desiccation of the sample in situ. Rapid and complete desiccation minimizes the possibility of sample breakdown due, for example, to microbial presence. Following sample application, the testing device is returned to a physician or testing laboratory for completion of the test process.

Given the description which follows, one of skill in the art will recognize that the testing element or elements may be provided in an array of alternative embodiments. Referring to the immunochromatographic embodiment, for example, a required element of the test strip is a liquid-conductive solid phase material to which a detection reagent (described above as the second specific binding reagent) may be immobilized. This solid phase material is preferably nitrocellulose. Nitrocellulose is a charged matrix to which an appropriately charged reagent, such as a monoclonal antibody, may be immobilized without prior chemical treatment. Alternatives such as filter paper may also be used, however, chemical coupling (e.g., GNBr coupling) is required to attach a charged reagent such as an antibody to a matrix of this type.

A preferred liquid-conductive solid phase material is a nitrocellulose membrane having a pore size of at least about 1 micron. Nitrocellulose membranes best adapted for use in connection for immunochromatography of this type have a pore size of about 5–20 microns. The selection of particular pore size dictates flow rate. Depending upon the particular application, a faster or slower flow rate may be indicated and an appropriate solid phase material is selected.

To facilitate handling, it is desirable to provide a backing to the nitrocellulose membrane. A thin plastic sheet stock (e.g., lexan or polystyrene) may be cut to provide a suitable water resistant backing for the solid support. Such sheet stock is selected so as not to interfere with the reading of a test result. For example, the selection of a white or clear sheet stock is generally preferred. In an alternative embodiment, the liquid conductive solid phase material may be sandwiched between such water resistant sheet stock.

When inserted into the housing, the or each test element is designed to communicate with the sample application matrix. Although this communication may be direct between the sample application matrix and the liquid-conductive solid support, in a preferred immunochromatography embodiment, additional elements are incorporated. For example, a conjugate pad may be provided. In use, the conjugate pad is disposed between the sample application matrix and the liquid-conductive solid support of the testing element. As will be discussed in greater detail below, the conjugate pad provides a matrix for the deposition of a labelled detection reagent which is free to migrate when rehydrated (the first specific binding reagent in the brief review of immunochromatography provided above). The sample is desiccated within the sample application matrix prior to the insertion of the testing element. At the time of rehydration during the testing step, the labelled detection reagent within the conjugate pad is also resuspended and resolubilized. If analyte is present in the sample, the labelled reagent binds to the analyte and the complex is carried along with the solvent front to the detection zone of the testing element. While the conjugate pad may communicate directly with both the liquid-conductive solid support and the sample application matrix, additional elements may be incorporated as discussed in the Description of Preferred Embodiments Section which follows.

At the end of the testing element distal to the sample application matrix when in use, an optional absorbent pad is attached, in communication with the liquid-conductive solid phase material. This pad provides a solvent sink which drives the migration of the liquid sample through the detection zone. It is important that the absorbent pad have sufficient volume to drive the migration to the extent that substantially all unbound labelled detection reagent is carried beyond the detection zone of the testing element. One of skill in the art will recognize that an absorbent pad is a non-essential element. The need for this element can be obviated, for example, by extending the length of the liquid-conductive solid phase material beyond the detection zone such that a sufficient volume is carried through the detection zone.

In use, a sample is applied to the sample application matrix, preferably through an aperture in the housing which is in direct communication with said matrix. The sample is applied to the sample application matrix in a conventional manner. For example, a fecal smear may be applied to the sample application matrix. Alternatively, toilet bowl water may be sampled using an absorbent swab. In the latter sampling method, a short time may be allowed for hemoglobin to diffuse from the stool prior to sampling, or the swab may be used to disperse the stool into the toilet bowl water. The swab is then used to sample the water and transfer it by touching or "painting" the sample collection matrix. The liquid sample transferred is typically nearly colorless.

Depending upon the nature of the analyte, the testing device with sample applied may be stored in this form for a period of days, weeks or months prior to testing. To determine the presence of an analyte, the sample is rehydrated by adding an appropriate solution to the sample application matrix. The solution can be added through the same housing aperture(s) through which sample was applied. However, in most instances it is preferable to provide a second aperture, or aperture series, in the housing through which solvent is applied. This second aperture, or aperture series, is also in communication with the sample application matrix. Preferably, solvent applied through a solvent application aperture must migrate through the region of the sample application matrix where sample was actually applied, prior to reaching the point on the sample application matrix which communicates with the testing element.

The labelled detection reagent may be introduced into the immunochromatography assay in a variety of ways. For example, the labelled detection reagent may be solubilized in the solution used to rehydrate the contents of the sample application matrix prior to the resolubilization of the sample components. Alternatively, as discussed above, the labelled detection reagent may be introduced in solution into the conjugate pad and desiccated in situ. In this embodiment, the labelled detection reagent is resolubilized as the resolubilization solution migrates from the sample application matrix to the testing element. In yet another embodiment, a solution containing the labelled detection reagent may be added to the sample application matrix prior to the application of the sample. This solution is then desiccated in situ. In this embodiment, analyte of interest, if present, and labelled detection reagent will be solubilized from the dry sample application matrix at the time of testing.

Of the embodiments described in the preceding paragraph, the use of a conjugate pad is preferred for most embodiments. The addition of the labelled detection reagent to the resolubilization solution prior to sample resolubilization has the disadvantage of using the expensive detection reagent (which could require storage at 4° C.) in an inefficient manner. With respect to the desiccation in situ of the labelled detection reagent in the sample application pad prior to sample application, this would result in the establishment of a test device in which the housing element is dedicated to a particular assay. One of the many benefits of the disclosed device is the fact that the housing (together with other elements of the device excluding the testing element) is totally generic. Thus, the test housing component of the testing device can be purchased in bulk and stored as needed for any of a variety of testing requirements. The relatively expensive test-specific component is the testing element which can be selected for a particular need and used in conjunction with the generic housing.

Preferably the labelled detection reagent is a monoclonal or polyclonal antibody specific for a first epitope of the analyte of interest, coupled to a detectable label. The detectable label can be coupled to the antibody by any of the applicable techniques known in the art including, for example, covalent bonding and passive adsorption.

The detectable label may be a direct or an indirect label. A direct label is a label which is readily visible in its natural state, either to the naked eye, or with the aid of optical devices. A label which is visible only in the presence of external stimulation, such as ultraviolet light, is also considered to be a direct label. Examples of direct labels include dye sols (e.g., colloidal carbon), metallic sols (e.g., gold and iron), fluorescent particles and colored latex particles.

Indirect labels require the addition of one or more developing reagents, such as substrates, to facilitate detection. Such labels include, for example, enzymes such as alkaline phosphatase and horseradish peroxidase.

The immobilized capture reagent is also typically a monoclonal or polyclonal antibody which is specific for a second epitope or range of epitopes on the analyte of interest. Thus, analyte present in the sample, whether bound by the detection reagent or not, is bound by the immobilized binding reagent in the detection zone. In a case in which a direct label is employed, a visible line appears on the liquid-conductive solid support as bound label accumulates in the detection zone. The appearance of this line may be diagnostic for the presence of analyte of interest in the sample.

An optional control zone can also be integrated into the testing element. The function of a control zone is to convey an unrelated signal to the user which indicates only that the testing process is complete and that the binding interaction which results in the detectable unrelated signal has taken place as expected. For example, the control zone may comprise an "anti-mouse" polyclonal antibody immobilized to the liquid-conductive solid phase material, preferably downstream of the detection zone. Assuming that the detection reagent is a murine monoclonal antibody linked to a detectable label, detection reagents not bound in the detection zone through a sandwich interaction involving the analyte of interest will ultimately bind in the control zone. In the absence of a signal in the detection zone, a control zone signal would indicate to the user that, for example, the sample contained nothing that resulted in general interference with an immunological assay. It can be imagined, for example, that extremes of pH or salt concentration could result in general interference through conformational changes or physical destruction on one or more of the participants in the immunologically based interaction to be detected. The inclusion of a control zone functions to provide a degree of confidence with respect to such variables.

The analyte of interest is determined in advance to be one which is diagnostic of a particular condition. For example, in connection with POB tests, the analyte of interest is preferably human hemoglobin.

The method and apparatus of the present invention is applicable to detecting analytes in humans and other animals. Other animals include primates, livestock animals (e.g. cows, sheep, horses, donkeys, pigs), laboratory test animals (e.g. rabbits, mice, rats, guinea pigs, hamster), companion animals (e.g. dogs, cats) and captive wild animals. The present invention also extends to detecting analytes in plants (e.g. monocotyledons and dicotyledons) and other life forms (e.g. microbes, yeasts, fungi, moulds). The present invention may also be used to detect analytes in geographic and industrial locations, including soil, oceans, rivers, water storage regions, toxic waste dumps, building sites, mining areas (e.g. coal, bauxite, uranium, graphite amongst many others) as well as in the air. The health status of humans, and other animals or plants or other life forms may be deduced or determined in the presence or level of analyte or by the absence of analyte. The environmental status may also be ascertained such as determining the presence of contaminants in various geographic or industrial locations.

BRIEF DESCRIPTION OF THE DRAWINGS

FIG. 1 is a perspective view from the front of the device of the present invention.

FIG. 2 is a perspective view from the rear of the device of the present invention.

FIG. 3 is an exploded cross-sectional view of the testing element of the present invention.

FIG. 4 is a cross-sectional view of the device of the present invention as taken along line 4—4 in FIG. 2B.

DESCRIPTION OF PREFERRED EMBODIMENTS

Figure 5:
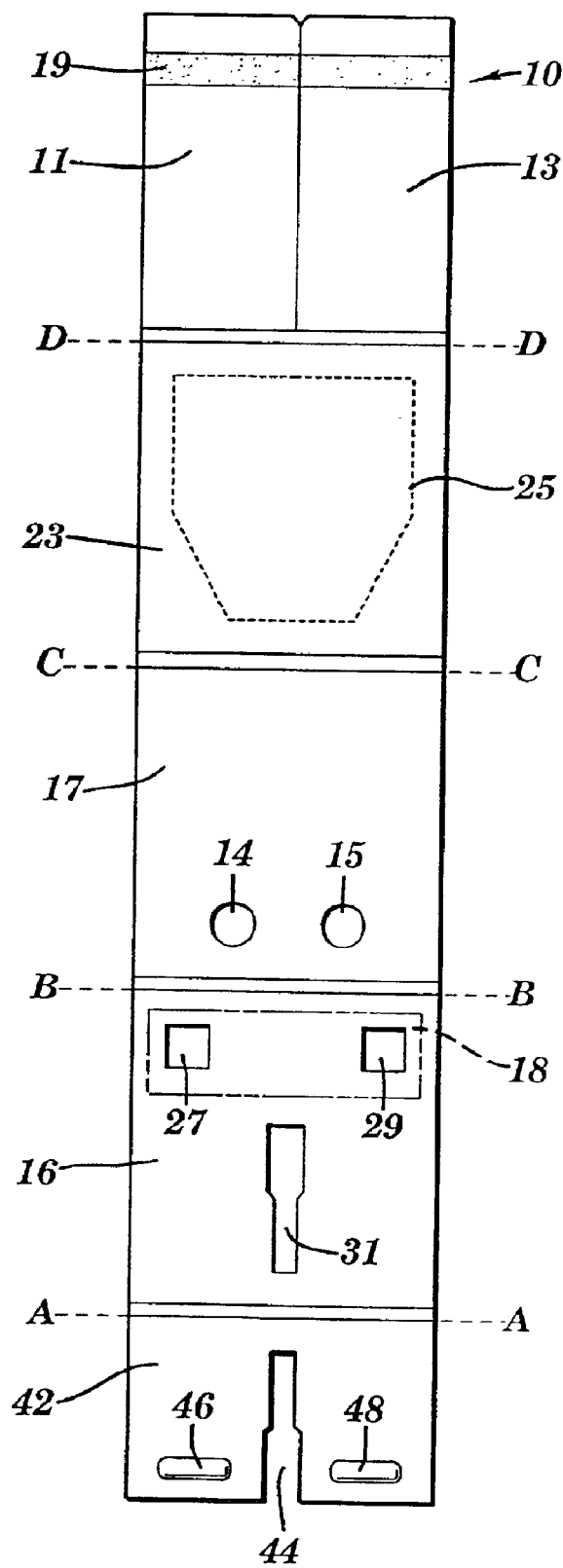
FIG. 5 is a top view of the device of the present invention as shown in pre-folded form.

By way of example only, certain preferred embodiments of the invention will now be described in detail with reference to the accompanying drawings.

Referring to FIG. 1, the testing device of the present invention is shown as configured for the detection of fecal occult blood in stool by immunochromatographic methods. FIG. 1A shows the device of the present invention with a front panel cover (10) comprising two sample application cover flaps (11 and 13) in the closed position. By raising flap (11), a patient exposes a first sample application aperture (14) in the front panel (17) of the device (FIG. 1B). The first sample application aperture is in communication with a sample application matrix (18) (shown in FIG. 4). Sample is applied to the sample application matrix (18) via the sample application aperture (14). Following application of the sample, cover flap (11) is closed and sealed. A pressure sensitive adhesive with a removable backing strip (19) is provided for this purpose. The process is then repeated on a second consecutive day and sample is applied via the sample application aperture located behind flap (13). While the embodiment shown in FIGS. 1A and 1B has only two sample application apertures, this is intended to be non-limiting. The sealed testing device is then forwarded to a doctor's office or testing laboratory for determination of test results.

Upon receipt, a technician at the doctors office or testing laboratory opens the testing window (25) located on the rear panel cover (23), as show in FIG. 2A. Perforations are provided for the opening or removal of the testing window to facilitate access. Opening or removal of the testing window (25) reveals several apertures which characterize the rear panel (16). These include solvent application apertures (27 and 29) and testing element insertion aperture (31). A testing element (33) is then inserted into the testing element insertion aperture (31). The testing element (33) contains a reagent enabling the detection of the analyte of interest in the sample.

The testing element is shown in exploded cross-section in FIG. 3. The testing element is comprised of a liquid-conductive solid phase material (35) which is preferably nitrocellulose membrane. To facilitate handling, a backing sheet (39) is provided. Non-absorbent plastics such as lexan or polystyrene are preferred backing sheet materials. Preferred embodiments also include one or more layers of high capacity liquid conducting material referred to herein as "bridging layers". A bridging layer (38) is shown in FIG. 3. In the embodiment of FIG. 3, a conjugate pad (37) is disposed between bridging layer (38) and the liquid conductive-solid phase material (35). As discussed above in connection with preferred immunochromatographic embodiments, the conjugate pad contains labelled detection reagent desiccated in situ. An absorbent pad (41) is also provided as a component of testing element (33). The absorbent pad (41) functions as a solvent sink thereby driving the migration of the solvent front. The elements shown in FIG. 3 are assembled using a non-water soluble adhesive. It will be evident that the overlap of elements such as bridging layer (38) and conjugate pad (37) creates a progressive wedging effect which results in good liquid conductive contact between the sample application matrix (18) and the testing element (33), following insertion of the testing element (33) into the testing element insertion aperture (31). Immobilized capture reagent is attached to the liquid-conductive solid phase material thereby creating a detection zone (43) on testing element (33).

FIG. 4 is a cross-Section of the device with the testing element (33) inserted. FIG. 4 shows many of the previously discussed elements including, for example, testing element (33) and individual components thereof (absorbent pad (41), liquid-conductive solid phase material (35), conjugate pad (37), bridging layer (38) and backing sheet (39)); sample application cover flap (13); front panel (17) with sample application aperture (15); rear panel (16); rear panel cover (23) with testing window (25); and sample application matrix (18). Also shown is an optional element not previously discussed. This optional element is referred to as a spacer panel (42). The spacer panel, which is shown in greater detail in FIG. 5, functions to create a testing element insertion void space between the sample application matrix (18) and the front panel (17) in the assembled device. Spacer panel (42) includes a second testing element insertion aperture (44) and embossed point (48) also shown in FIG. 5. As shown in FIG. 4, when testing element (33) is inserted, it occupies this testing element insertion void space. The progressive wedging referred to previously in connection with FIG. 3 results in good liquid-conductive contact between the sample application matrix (18) and the testing element (33).

Again referring to FIG. 4, following insertion of the testing element, the technician rehydrates the sample by adding a solvent to the sample application matrix (18) via solvent aperture (29) in rear panel (16). The solvent solubilizes sample components in the sample application matrix (18) and carries the solubilized components through bridging layer (38) and into the conjugate pad (37) with the solvent front. In the conjugate pad (37), labelled detection reagent is solubilized and binds to analyte if present in the sample. The solvent front, and any soluble materials carried with the solvent front, then move on to the liquid-conductive solid phase material (35). If analyte is present in the sample, a visibly detectable complex comprising analyte, labelled detection reagent and immobilized capture reagent forms in detection zone (43).

In a preferred embodiment, front panel cover (10), rear panel cover (23), front panel (17), rear panel (16) and spacer panel (42) are produced from a single sheet of stock by appropriate cutting and folding. Referring to FIG. 5, a generally rectangular sheet of stock is provided. Solvent application apertures (27 and 29) and a testing element insertion aperture (31) are cut in rear panel (16). Sample application apertures (14 and 15) are cut in front panel (17). The outline of the diagnostic window (25) is perforated in the rear panel cover (23). The front panel cover (10) is cut to from two flaps (11 and 13) which will seal the sample application apertures following sample application. Pressure sensitive adhesive (19) is provided for sealing sample application cover flaps (11 and 13). Spacer panel (42) is cut to provide a second testing element insertion aperture (44). In addition, the spacer panel (42) is optionally embossed at embossed points (46 and 48). As an alternative to embossed points (46 and 48), optional spacer elements may be attached to spacer panel (42) using an adhesive. The function of the optional embossed points (46 and 48) or the alternative optional spacer elements, is to increase the testing element insertion void space between the sample application matrix (18) and the front panel (17) in the assembled device, if desirable. Whether or not to include such optional elements depends, for example, on the relative thicknesses of the sample application matrix (18) and the stock from which the housing is produced. Folds, are made along lines D—D, C—C, B—B, and A—A to form the housing. Prior to folding, the sample application matrix is appropriately positioned and adhesive is applied in appropriate locations to aid in maintaining the relationship of elements in the folded housing.

Figure 6:
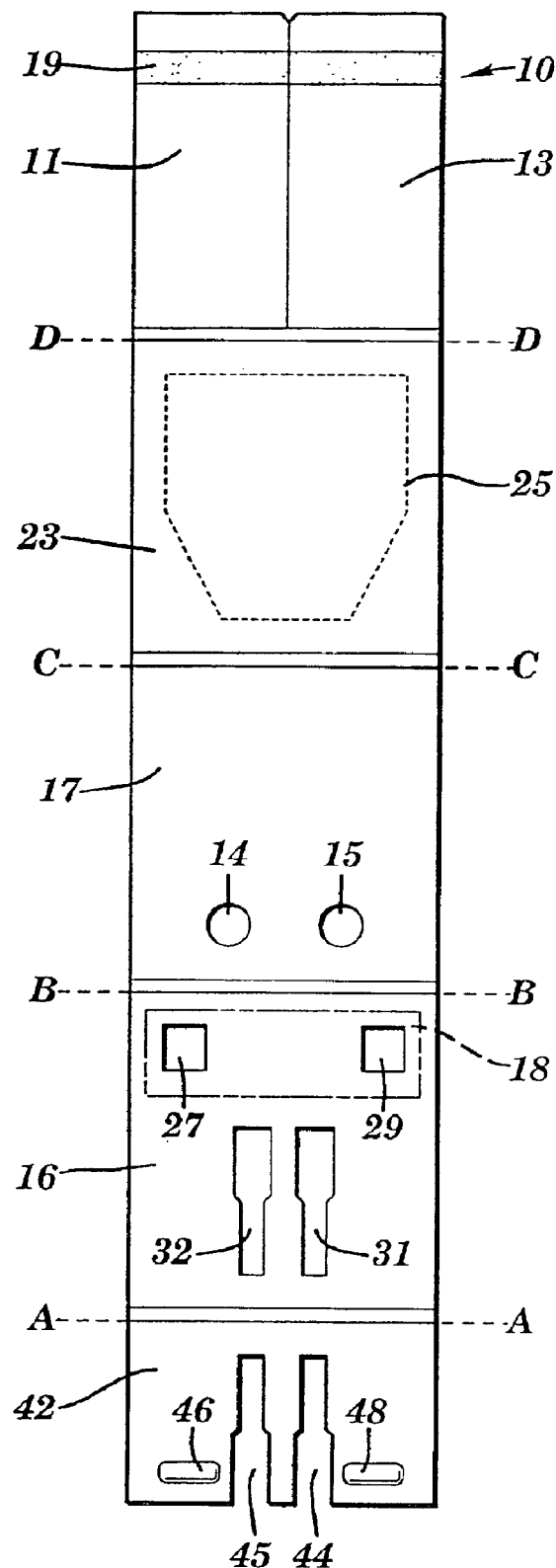
FIG. 6 is a top view of an alternative embodiment of the device of the present invention, shown in pre-folded form.

An alternative embodiment of the device of the present invention as described in detail in FIGS. 1 to 5, incorporating more than one insertable testing element, is shown in FIG. 6. In this embodiment the rear panel (16) is provided with two testing element insertion apertures (31,32) and the sample application matrix (18) is configured so as to provide good liquid conductive contact between the sample application matrix (18) and individual testing elements (33) inserted into each aperture (31,32). The spacer panel (42) includes two second testing element insertion apertures (44,45) corresponding in position to apertures (31,32) so that individual testing elements (33) each occupy the testing element void space as previously described, and are each in good liquid-conductive contact with the sample application matrix. Of course, similar devices may be configured for use with more than two insertable testing elements. As previously described, in this alternative embodiment, the two or more insertable testing elements (33) may be the same (providing replicate tests of the same sample applied to the sample application matrix), or they may be different testing elements (so as to provide different tests of the same sample applied to the sample application matrix). In a particularly preferred embodiment for use in FOB testing, one element may be a guaiac-based testing element and another element may be an immunochromatographic testing element.

In addition to the accumulation and aggregation of samples of discrete temporal origin (i.e. samples taken on separate days) as discussed hereinabove, the present invention may advantageously be utilized to accumulate and aggregate samples of discrete spatial and/or biological origin.

An example of spatially distinct samples includes soil and/or ground water samples obtained from various distinct geographic locations and/or sources. In this manner, in addition to the above described medical diagnostic applications, the present invention may be used in non-medical testing, such as for detecting environmental toxins.

Examples of biologically distinct samples include urine, blood, sweat and saliva samples, which may be particularly useful in applications such as drug screening, in which a particular analyte may be present in one or more of such samples.

The samples may be applied in substantially any form, i.e., liquid or dried, and may be applied to one or more locations of the sample application matrix 18. For example, several sample application apertures (14, 15, etc.) may be provided, with a single sample being applied to each aperture. Alternatively, a plurality of samples may be applied to a single application aperture. In this regard, liquid samples may be mixed in a separate device (i.e. a test tube), prior to application to a sample aperture. Similarly, it may be possible to apply multiple liquid samples sequentially to a single application aperture. In one example of this approach, the liquid samples may be permitted to dry in situ prior to application of subsequent samples.

Subsequent liquid samples also may be applied to the matrix without waiting for earlier applied liquid samples to dry, such as with an eye dropper, etc., whereby the liquid samples will be absorbed by the matrix. These mixed, liquid samples may be subsequently desiccated in situ. One skilled in the art will recognize that the number of samples capable of being applied in this manner is limited by the porosity and volume of the matrix, i.e. additional samples may not be applied once the matrix is fully saturated.

Similarly, dried or solid samples, e.g. samples dried on paper discs, may be accumulated by stacking the discs within a single aperture. Subsequent application of liquid to hydrate the matrix solubilizes the samples, permitting them to pass through the porous paper disc material and aggregate in the manner described hereinabove.

Usage of the invention as so described advantageously enables identification of intermittently expressed analytes, as in the case of multi-day FOB testing for intermittent bleeding. In addition, the invention enables successful screening in the event analyte levels are low, perhaps below the threshold of detection for a single sample, by aggregating the signal generated by multiple samples to bring it up to detectable levels.

Persons skilled in the art will recognize that any combination of the aforementioned samples, such as any combination of liquid and dried samples, of distinct temporal, spatial, biological and/or non-distinct origin, may be applied to a single or multiple locations on the sample application matrix, without departing from the spirit and scope of the present invention.

EXEMPLIFICATION

Construction of Testing Device

Test elements were manufactured by laminating the following components to a white plastic support (high impact polystyrene, 0.5 mm), coated on one surface with adhesive (3M, St. Paul, Minn., #465 transfer tape), as shown in FIG. 3:

1) nitrocellulose membrane (Millipore, Bedford, Mass., Type STHF0200, 18 mm) striped with monoclonal anti-human hemoglobin antibody at 2 mg/ml;
2) absorbent for absorbent pad (Ahlstrom, Mt. Holly Spring, Pa., Grade 904, 18 mm):
3) conjugate pad (General Polymeric, Reading, Pa., 25 micron UHMWPE skived tape, 10 mm) infiltrated and dried in situ with polyclonal anti-human hemoglobin antibody conjugated to colloidal gold (EY Laboratories, San Mateo, Calif.); and
4) conductive paper for bridging layer (Ahlstrom, Grade 1281).

Following lamination, the web was slit at 6 mm intervals to form individual test elements.

Housings (73 mm×76.2 mm), as depicted in FIG. 5, were manufactured from waterproofed (polycoated) SBS cardboard. The sample application matrix (Porex, Fairbum, Ga., HDPE Type 4588) was applied to the rear panel of the housing with transfer adhesive (3M, #465).

Example 1

Human blood was diluted 1:10,000 and 1:100,000 in distilled water. For each of the dilutions of blood, and for a control sample of distilled water, 25 µl was added to each of the two sample application apertures of a testing device and allowed to air dry for two hours. 100 µl reconstituting reagent (P.B.S. containing 0.5% Bovine Serum Albumin, 1% Triton X100 and 0.1% sodium azide) was added to each solvent application aperture and a test strip inserted. A clear red line developed on the test strip with the two blood dilutions, i.e. positive detection, whereas the water sample gave no detectable signal (i.e. a negative result).

In an otherwise identical experiment, the same blood dilutions were added (25 µl for each) to Hemoccult (SmithKline Diagnostics, Palo Alto, Calif.) slides and a ColoCare (Helena Laboratories, Beaumont, Tex.) test pad (a device for detecting blood in the toilet bowl water that is added directly to the toilet bowl).

RESULTS

|  | $10^{-4}$ | $10^{-5}$ | Water |
|---|---|---|---|
| Hemoccult | + | − | − |
| ColoCare | + | − | − |
| Device of present invention, | + | + | − |

Example 2

Fresh human blood (50 µl) was added to the water in a toilet bowl (~2L). After full dispersion of the added blood, the water was sampled with a Dacron swab (Hardwood products, Guildford, Me.) and transferred to a Hemoccult card and to the sample application matrix of the device of the present invention. Following the sampling, a ColoCare pad was added to the toilet bowl and observed for any change in color.

Results

The device of the present invention readily detected the blood, whereas water taken from the bowl before the addition of the blood tested negative. The Hemoccult and ColoCare tests remained clearly negative with the water to which the blood had been added.

What is claimed is:

1. A testing device for the identification of an analyte of interest, comprising:
   a. a housing having a sample application matrix for:
      i. receipt of a liquid-containing sample;
      ii. desiccation of the sample in situ; and
      iii. rehydration of the desiccated sample for transfer to a testing element;
   b. at least one aperture in the housing to receive a testing element inserted therein and hold said testing element in direct liquid-conductive communication with the sample application matrix; and
   c. at least one insertable testing element, the or each testing element, on insertion into an aperture in the housing, being retained within the housing in liquid-conductive communication with the sample application matrix, such that upon rehydration of the desiccated sample, resolubilized or resuspended components of the sample are carried from the sample application matrix to the testing element or elements.

2. A testing device for the identification of an analyte of interest, said testing device comprising:
   a. a housing having a sample application matrix for receiving a plurality of samples at discrete locations thereon, and aggregating the samples;
   b. at least one aperture in the housing to receive a testing element inserted therein and hold said testing element in direct liquid-conductive communication with the sample application matrix; and
   c. at least one insertable testing element, the or each testing element, on insertion into an aperture in the housing, being retained within the housing in liquid-conductive communication with the sample application matrix, such that a single test may be performed to simultaneously determine presence of the analyte of interest in a plurality of samples having discrete origin.

3. The testing device of claim 2, wherein
   i. a liquid-containing sample is received by said sample application matrix;
   ii. the sample is desiccated in situ; and
   iii. the desiccated sample is rehydrated for transfer to said testing element or elements.

4. The testing device of claim 2, wherein a dried sample is received by said sample application matrix.

5. A testing device for the identification of an analyte of interest, said testing device comprising:
   a. a housing having at least one sample orifice selectively openable and sealable for admitting and sealably maintaining a plurality of samples therein, and at least one test orifice for insertion of a testing element or elements therein;
   b. a sample application matrix disposed within said housing in communication with said at least one sample orifice and said at least one test orifice, wherein:
      i. the plurality of samples are received by said sample application matrix; and
      ii. the plurality of samples are aggregated thereon, such that a plurality of samples of discrete origin may be applied and sealed within said testing device, and subsequently tested in the aggregate.

6. The testing device of claim 5, wherein the plurality of samples are received at a single location on said sample application matrix.

7. The testing device of claim 5, wherein the plurality of samples are received at discrete locations on said sample application matrix, and said matrix aggregates the samples upon said insertion of the testing element or elements.

8. The testing device of claim 5, wherein said housing has a plurality of sample orifices selectively openable and sealable for admitting and sealably maintaining the plurality of samples therein.

9. The testing device of claim 5, further comprising at least one testing element for insertion through the or each said test orifice for testing the plurality of samples.

10. The testing device of claim 5, wherein at least one of the plurality of samples contains liquid, and:
   the liquid-containing sample is desiccated on said sample application matrix in situ;
   the desiccated sample is rehydrated thereon; and
   resolubilized or resuspended components of said sample are aggregated with at least one other of the plurality of samples for testing.

11. A testing device for the identification of an analyte of interest from a plurality of samples, at least one of the plurality of samples containing liquid, said testing device comprising:

a. a housing having a sample application matrix for:
   receipt of the plurality of samples at discrete locations thereon;
   desiccation of the liquid-containing sample or samples in situ;
   rehydration of the desiccated sample or samples; and
   aggregation of solubilized or suspended components of the sample or samples for analyte analysis;
b. at least one aperture in the housing to receive a testing element inserted therein and hold said testing element in direct liquid-conductive communication with the sample application matrix; and
c. at least one insertable testing element, the or each testing element, on insertion into an aperture in the housing, being retained within the housing in liquid-conductive communication with the sample application matrix, wherein a single test may be performed to simultaneously determine presence of the analyte of interest in a plurality of samples having discrete origin.

* * * * *